United States Patent [19]

Landwehr

[11] Patent Number: 4,987,432
[45] Date of Patent: Jan. 22, 1991

[54] HUMAN TOPOGRAPHY THROUGH PHOTOGRAPHY

[76] Inventor: Ulrich M. Landwehr, Bahnhofstrasse 8, D-3000 Hannover, Fed. Rep. of Germany

[21] Appl. No.: 407,887

[22] Filed: Sep. 15, 1989

[30] Foreign Application Priority Data

Sep. 17, 1989 [DE] Fed. Rep. of Germany ....... 3831630

[51] Int. Cl.$^5$ .............................................. G03B 29/00
[52] U.S. Cl. ..................................... 354/77; 354/290; 354/62; 356/376; 356/359; 353/28
[58] Field of Search ................... 354/62, 75, 77, 78, 354/290; 353/28, 30, 40, 41, 94; 250/237 G; 356/376, 379

[56] References Cited

U.S. PATENT DOCUMENTS

| | | | |
|---|---|---|---|
| 4,070,683 | 1/1978 | Altschuler et al. | 354/77 |
| 4,370,039 | 1/1983 | Landwehr | 354/77 |
| 4,786,925 | 11/1988 | Landwehr | 354/77 |

Primary Examiner—Brian W. Brown
Attorney, Agent, or Firm—Ralf H. Siegemund

[57] ABSTRACT

An apparatus for acquiring the dimensions of an object by means of photography, particularly the topography of a human body, includes a still or video camera positioned to take pictures of the person is improved by a projector having a different orientation and projecting a line raster in a diverging beam; and a mirror intercepts the projection beam and provides a parallel beam wherein the horizontal line rasters as projected remain equidistant with no diverging direction; the mirror is preferably made of multiple strips but could be just a concave reflection.

9 Claims, 1 Drawing Sheet

U.S. Patent
Jan. 22, 1991
4,987,432
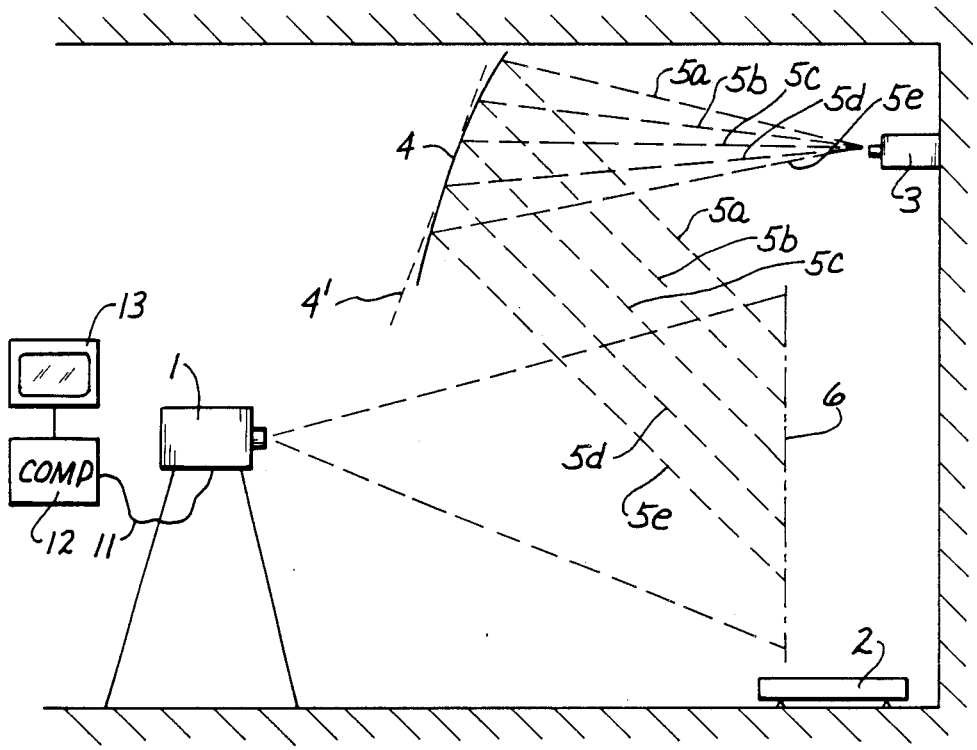
FIG. 1
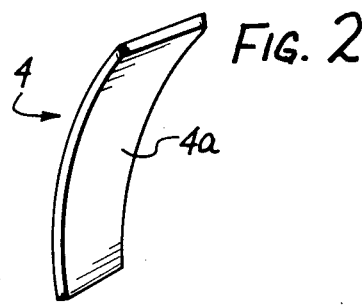
FIG. 2
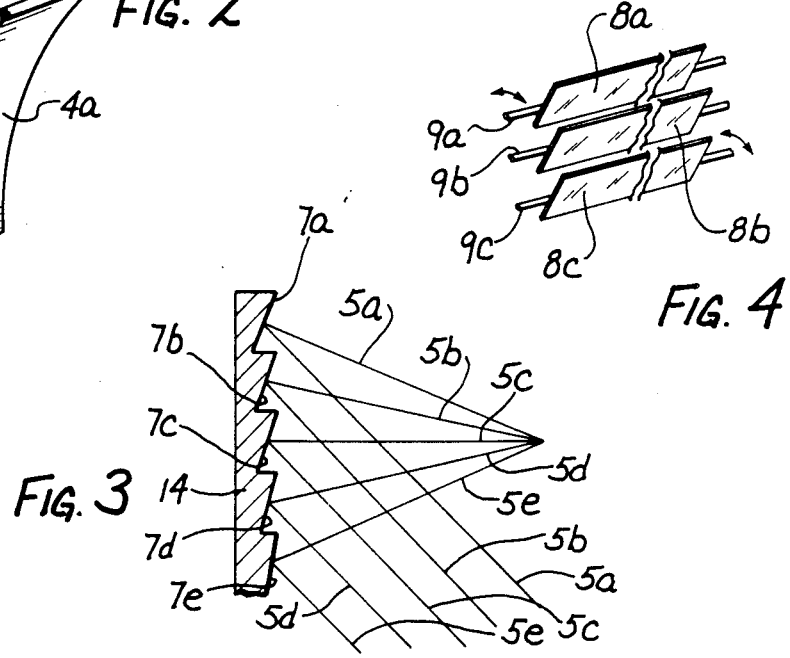
FIG. 3
FIG. 4

HUMAN TOPOGRAPHY THROUGH PHOTOGRAPHY

BACKGROUND OF THE INVENTION

The present invention relates to the acquisition and ascertainment of dimensions and measurements of an object under utilization of photographic method, and more particularly the invention relates to photographically acquired dimensions and measurements of the contour (topography) of a human body.

Topographic method and equipment is known wherein a photographic image of an object that is the subject of measurement and dimensions acquisition, is taken together with a measuring raster in superimposed relationship e.g. as double exposure; and during the taking of the picture horizontal lines are projected onto the object. The reflection of these lines will be distorted of deflected up or down by any unevennesses of the surface of the object. These distortions in relation to the measuring raster give then a measurement of the third dimension.

A method and equipment of this kind is for example shown in U.S. Pat. No. 4,370,039 corresponding to German patent No. 29 48 010 and U.S. Pat. No. 4,639,107 corresponding to German patent No. 34 25 913. Both references show a projection of the horizont lines from above and oblique as far as the object plane of the object is concerned in order to make visible the three dimensions by up or down deflection of the horizontal raster lines. The drawings in the first mentioned patent indicate particularly this capability. For example if a horizontal line is deflected up the local topography of the object is closer to the camera i.e. it indicates a bulging stomach or in case of a down deflection the indication is that of an indent. The measuring raster which is superimposed in the form of a double exposure then in relation to the visible and deflected projection lines permits an accurate measurement concerning all three dimensions.

The line pattern is projected through a slide and flash light projector. This particular method is highly practical and has however the disadvantage that in the case of a tall person it may be necessary to consider the fact that the angle of projecting the line pattern is variable one. Usually it is practical to have the center axis at an orientation of 45 degrees to the vertical but there are then considerable parts of the projection which impinge upon the body at a larger angle such as the head area while the legs receive projection of line pattern that is much shallower angle less than 45 degrees. This in turn requires establishing a recalibration and to provide a relatively complicated algorithm in order to offset this variation. While possible in principle it was found that the digitalization is really a significant problem.

In order to offset this draw U.S. Pat. No. 4,786,925 corresponding to German patent No. 36 21 927 proposes a plurality of such projectors all with projections axes that run in parallel and all e.g. 45 degrees to the vertical. Deviations from the average angle are in fact very small and introduce a negligible error only. The projection as a whole and then the reflection of the projected lines do indeed present a very accurate topographic picture of the body. Unfortunately the equipment cost for this procedure is very high and there is definitely a need for simplification in terms of economy.

DESCRIPTION OF THE INVENTION

It is an object of the present invention to provide a new and improved method and equipment of the kind referred to in the introduction such that the deviation from an average protection angle such as 45 degrees is minimal without incurring the costs and expenses of multiple projectors.

It is a particular object of the present invention to improve the earlier equipment of the kind of interest towards elimination of the distortion resulting from deviation in the projection of the horizontal line raster without however foregoing the simplicity of the earlier equipment In accordance with the preferred embodiment of the present invention it is suggested to provide a single projection of a line raster but not directly towards the object plane and the object onto which the line raster is to be projected, but towards a curved or inclined mirror or a combination of curvature and inclination or of a variable inclination such that the lines as reflected are now reoriented in a parallel beam or plural parallel beams all being directed at 45 degrees towards the object or any other suitable angle which is the same for all beams so that a quasicollimated beam is produced for projection directly onto the object to be subject to the photographic measurement.

As a consequence of the inventive features there is a similarity in the projection direction as to each of the horizontal lines. The known earlier equipment needs to be augmented by that specific kind of reflector which is considerably more economical as compared with multiple projections. Therefore the equipment deviates from the one shown in U.S. Pat. No. 4,370,039 in that projector and camera though in different levels face each other, and a mirror or reflecting surface(s) intercept the projection beam, to redirect a near collimated beam of the line raster onto the object at a specific angle such as 45 degrees. The essential part of the invention is that each horizontal line (or two or three lines) as projected is intercepted as far as the projector is concerned, by a different mirror or mirror portion, the difference being in the inclination in relation to the average axis of projection which is preferably horizontal. Owing to this deviation in projection as to each horizontal line they all are redirected and become parallel as far as projection is concerned, towards the object such as a person that (who) is subject to the measurement.

It is a particular advantage to provide the mirror as a plurality of striplike elements and each of the elements is particularly adjusted with regard to the longitudinal axis. Ideally there is one striplike element per horizontal line to be reflected but it was found that for practical purposes two or three lines may be intercepted by a mirror of the same orientation even though from the projection point of view the angle of projection of each of these three lines differs little from the other but the difference is for many cases of application simply of a negligible nature. Essentially this of course has to do and is strongly related to the number of horizontal lines being used which gives the resolution of the measuring raster and one does not have to provide for a greater projection accuracy than attainable by the raster itself.

The elements each being provided as a mirror may be mounted on their narrow sides individually in holders and each holder is adjustable around a horizontal axis all of them being parallel to each other and at right angles to the projection axis as well as to the camera axis. Alternatively, the mirror strips may be all on a common backing. This very advantageous configuration for practicing the invention uses a mirror which is not curved but has in a plane transverse to the reflection plane a sawtooth pattern with a variation in the inclination of the teeth and in order to offset the divergence of the projection beam so that each of the little mirror striplets produced in this fashion produces basically a beam that is parallel to the one produced by the one next to it and so forth.

In a different form one can use a cambered plate which is arranged at about 22.5 degrees on the average to the vertical; the curvature of this mirror plate is dependent of the focal length of the projection objective. The angle of 22.5 degrees is taken between the tangent on that portion of the mirror which is intercepted by the axis of the projector. The specific angle is of course given by the angle between that tangent and the vertical.

The camera that is being used for taking up the picture is preferably a videocamera with a horizontal scan, that is a scanning in a pattern which runs direction equal to the direction of the horizontal line pattern. This facilitates processing of the signals and the output of the video camera is connected to a computer and/or a video monitor. In this case then it is preferred not to use a flash projection for the line pattern but the regular continuous one.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a schematic side view of the system in accordance with the preferred embodiment of the present invention for practicing the best mode thereof;

FIG. 2 illustrates a first example for realizing the reflector used in the equipment shown in FIG. 1, the drawing is in a perspective view;

FIG. 3 is a cross section through a modification; and

FIG. 4 illustrates another example for realizing multiple reflection striplets.

Proceeding now to the detailed description of the drawings, FIG. 1 illustrates a camera 1 being e.g. a photographic camera or a video camera which is connected, as is schematically indicated by line 11, to a computer or processor 12. Reference numeral 13 schematically indicated the utilization of a monitor. The entire arrangement is placed within a room as schematically indicated by cross hatching showing one wall, a floor and a ceiling.

Reference numeral 2 refers to a balancing plate 2, the person which is the object to the topographic body measurement will stand on the balancing plate 2 of the kind shown e.g. in Canadian patent No. 1,227,632, in the German patent No. 2,948,010 or in U.S. Pat. application Ser. No. 186,621, filed 04/27/1988 (see also other literature mentioned in the latter application). My above mentioned patents refer to the additional projection of a measuring raster by means of the camera 1 or in different cameras whereby the combination for double exposure purposes is specifically disclosed. U.S. Pat. Ser No. 109,080, filed 10/16/1987 (allowed) on the other hand shows the incorporation of a measuring raster equipment into the camera. My above mentioned application Ser. No. 109,080 is equivalent to German patent application 36 32 450.

The measuring raster actually could be provided through the computer in which case the video camera 1 is one that provides a measuring raster without projection but internal processing superimposes that raster on the image that is produced. In this case a measuring raster projection in optical sense is not necessary but may result simply through data processing and in combination with the video.

Irrespective of whether 1 is a regular camera or a video camera, a projection of a horizontal line raster is provided for by means of a projector 3. In the case of a video camera as mentioned above the projector 3 should be continuous one if 1 is a regular camera, 3 is a flash projector. The projector 3 is mounted on the wall and faces the camera though at a different horizontal level which is a question of orientation that has nothing to do with the question whether or not the projector 3 is a continuous one or a flash projecting one.

The optical axis of the projector 3 is oriented horizontally and so is the optical axis of camera 1. The projector 3 projects towards a mirror 4, different examples of which will be described below. With reference to FIGS. 2, 3, 4. Presently it is assumed that in a simple form this mirror is just concave mirror with a line 4' denoting a tangent on that point in the mirror which intercepts the optical axis of the projector 3 and that tangent 4' has an angle of 22.5 degree to the vertical.

The concavity of the mirror 4 in relation to the projector 3 as far as distance is concerned and in further relation to the optical data including the focal length of the projector lens are so chosen that the various beams such as 5a, b, c, d, e, being originally of a divergent nature are collimated. In other words only the beam 5c is approximately horizontal along the axis of the projector 3 while different angles to the horizontal exist as far as the beams 5a, 5b, and 5d, 5e on the other hand are concerned. All these beams are now reflected by the reflector 4 and end up in a parallel configuration as can be seen from the drawing. The function of the mirror 4 is to provide for all of these beams an angle of projection which is similar. In the present case on account of the particular orientation chosen the angle is 45 degrees to the vertical.

FIG. 1 can also be interpreted differently. The lines 5a–5e could be regarded as beams of projection of horizontal raster lines which lines of course extend transversely to the plane of the drawings. Therefore owing to the this particular kind of projection and let 6 be an intercepting plane onto which hypothetically is made a projection, even though physically there may be nothing in that plane, it can be seen that these lines as so projected appear equidistantly spaced in that plane 6 on account of the parallelism of the beams as reflected by the mirror 4. Consequently the horizontal raster lines are equidistantly spaced in that plane and as measuring lines fulfill the desired function.

Line 6a is an assumed unevenness and one can see that the reflection of a horizontal line is shifted up for a forward bulging portion in relation to camera 1, and a horizontal line is shifted down for a rewardly bulging portion. Owing to the particular equidistance of the measuring raster and horizontal line pattern as so projected no conversion is necessary but the up and down shift of a line or of a portion thereof, is directly translatable into distance in one or the other direction from the plane 6.

In order to provide an exact positioning to plane 6 as a plane of reference that plane has of course a definite relationship to the standing plate 2 on which some object such as the person is placed. A suitable measuring scale may also be provided extending let us say horizontally in the plane 6 in inches or cm and giving a scale value in the vertical and with reference to the horizontal lines as projected in the plane 6 if there is or were an interception. Up and down deflection of that pattern is translatable as forward or rearward topography for purposes of completion should be mentioned that there may be plummet line to make sure that a vertical orientation is definitely established as a principal point of reference, and anything can be oriented in relation to that particular line including the measuring equipment and any scale in the field of view of plane 6 of the camera 1. This particular plummet line is also right in the middle of the orientation and one can say e.g. that the plummet line in the original set up should be such that it intercepts the optical axis of camera 1 which of course is in the center of the field of view. It there is a video camera then the entire equipment can be adjusted in relations thereto. For example the plummet line may be the standard point of reference, and the standing plate 2 is shifted laterally in relation thereto, so is the camera 1, to orient all the equipment in relation to each other so that whatever scale raster is projected and visible is quantitatively meaningfull.

The angle of incidence of 45 degrees to the vertical as provided by the beams 5a-5e in relation and onto the plane 6, is a practical and useful value but there is no inherent restriction requirement towards that particular value. Therefore the projector 3, or mirror 4 or both may be provided to be pivotable about horizontal axes which extend transversely to the plane of the drawing of FIG. 1. The pivoting may be provided motorically or manually. In the case of a motoric adjustment there may be remote control. Of course in the case of such a tilting the aligned spacing of the lines as projected into the plane 6 will vary and one needs a different slide that is being projected by the projector 3, or there is corresponding compensation operation in the processing of the video signal in computer 12.

FIG. 2 shows a mirror 4 in a perspective view with a surface 4a that is appropriately curved. Of course if the projections by projector 3 is a cylindrical one as far as the projection lens is concerned then the curvature needs to be in one plane only. Otherwise one does need a spherical curvature in order to provide for the requisite parallelism in the beam and the lines as projected.

FIG. 3 illustrates section through a particular mirror for a very advantageous configuration. The body so to speak of the mirror 14 is straight but it has a plurality of inclined reflecting surfaces such as 7a, 7b. . 7e etc. which together establish a sawtooth section but the "teeth" are differently oriented owing to a difference in inclination of these surfaces 7a, 7b etc. They have different inclination in relation to the overall extension or the backbody of the mirror 14 whereby specifically the angle of inclination in relation to the vertical decreases in down direction as can be seen directly from the drawing.

FIG. 3 shows also the interception pattern as far as the projection beams 5a, 5b. . . are concerned. The result is again a plurality of parallely oriented beams which again can be interpreted to be the projection of horizontal raster lines. In this case a corrective or corrected slide is not needed even if one tilts the mirror 4 about a horizontal axis.

The assumption has been made in FIG. 3 even interpreting the lines 5a, 5e, 5c as the projection of a horizontal raster lines that there is one line per mirror surface 7a, 7b, 7c etc. This is not necessary in all cases. A more economic way of proceeding as to provide two or three projecting lines per sawtooth and per reflecting surface 7a, b, etc. There is of course some deterioration in accuracy which is simply a matter of requirements concerning accuracy on one hand and an economic tradeoff on the other hand.

FIG. 4 illustrates an arrangement which as far as mirror surfaces are concerned is similar to FIG. 3 except each individual mirrors are small slats 8a, 8b and they are individually adjustable (rotatable) so as to meet the respective requirements. The adjustment is by way of tilting around the respective axes 9a, 9b. . as indicated by double arrow. In the case of FIG. 4, the projection must be a cylindrical one.

In all these cases it should be realized that the reflective surfaces can be made in a rather simple manner e.g. simply through casting a particular contour body. This is particularly the case as far as FIG. 3 is concerned. By way of silver depositing through a vapor depositing process, one provides for the requisite mirror and reflecting surfaces.

The camera 1 as well as the plate 2 may be coupled together and moved either together or in relation to each other to thereby provide a requisite positioning of the person and here the size of the person is to be accommodate through appropriate positioning. For example, in many cases of a human figure measuring of the torso of an adult person suffices. Here one really needs a total range vertical for viewing of about 90 cm which has to be covered by the horizontal line raster. In other words the lower and upper boundary as far as the projection field is concerned in the plane 6 is little under 1 m. The width is usually about 60 cm and the horizontal raster lines as projected into the plane 6 will have a distance spacing of about 1 cm. For different sections one can simply provide a change in the slides in projector 3 to reduce or increase the number of lines. The optics in the camera 1 may have to be adjusted either to a wide angle, a normal one or a telephoto lens just as the situation requires.

The invention is not limited to the embodiments described above but all changes and modifications thereof, not constituting departures from the spirit and scope of the invention, are intended to be included.

I claim:

1. Apparatus for acquiring dimensions of an object by means of a photographic or video camera, particularly topographic dimensions and contour of a human body and including, a camera means positioned to take still or video picture of the object such as a person and further including means for providing, from above and in an oblique direction of projection, a pattern of horizontal raster lines, the lines to be projected onto the object such as the person as being seen by said camera means, the improvement comprising:

a projector means having a different orientation than said oblique orientation and projecting in a diverging beam, said raster lines; and mirror means intercepting said projection beam and providing a parallel beam wherein the horizontal raster lines as projected remain equidistant to each other.

2. Apparatus as in claim 1 said mirror being a concavely curved mirror.

3. Apparatus as in claim 1 said mirror including a plurality of horizontally oriented by differently inclined mirror strips.

4. Apparatus as in claim 3 said mirror strips being part of a combined pattern of a sawtooth cross sectional configuration.

5. Apparatus as in claim 3 said mirror strips being established by individual mirror surfaces.

6. Apparatus as in claim 1 said camera being a video-camera.

7. Apparatus as in claim 6 said projector being a continuous projector.

8. Apparatus as in claim 1 said camera being a still camera.

9. Apparatus as in claim 8 said projector being a flash light projector.

* * * * *